United States Patent
Sharratt et al.

(10) Patent No.: US 8,439,929 B1
(45) Date of Patent: May 14, 2013

(54) METHOD OF PREPARING A GEL MATRIX FOR GRAFTING TO A BONE

(75) Inventors: Todd W. Sharratt, Stillwater, MN (US); Cathy Miller, Inver Grove Heights, MN (US)

(73) Assignee: Nordson Corporation, Westlake, OH (US)

( * ) Notice: Subject to any disclaimer, the term of this patent is extended or adjusted under 35 U.S.C. 154(b) by 248 days.

(21) Appl. No.: 12/942,113

(22) Filed: Nov. 9, 2010

Related U.S. Application Data (60) Provisional application No. 61/259,411, filed on Nov. 9, 2009.

(51) Int. Cl.
*A61B 17/58* (2006.01)
*A61B 17/60* (2006.01)
*A61F 2/00* (2006.01)

(52) U.S. Cl.
USPC ............................ 606/92; 606/93; 604/122

(58) Field of Classification Search ............ 606/92, 606/93; 604/122–125
See application file for complete search history.

(56) References Cited

U.S. PATENT DOCUMENTS 7,135,027 B2 * 11/2006 Delmotte ...................... 606/93
7,503,905 B2 * 3/2009 Jessop et al. .................. 604/122

* cited by examiner

*Primary Examiner* — Andrew Yang
(74) *Attorney, Agent, or Firm* — Wood, Herron & Evans, L.L.P.

(57) ABSTRACT

A method of preparing a graft material for a bone surface at a surgical site includes providing a first syringe having continuous side wall having an inner surface and an outer surface wherein the syringe has a first end and a second end wherein the inner surface defines a chamber. An adapter is removably attached to the distal end of the syringe wherein the adapter has a throughbore in fluid communication with the chamber. A first selected amount of solid bone graft material is disposed within the chamber. A plunger is inserted into the chamber to define a selected volume between a distal end of the plunger and the second end of the first syringe. A second syringe containing a selected amount of a liquid biomaterial is attached to the adapter wherein the second syringe is in fluid communication with the adapter and the first syringe such that the liquid biomaterial is transferred from the second syringe to the first syringe. After a selected amount of time, the biomaterial forms a gel matrix containing the solid bone graft material. The adapter is removed to provide an unobstructed opening at the second end and the plunger is depressed to force the gel matrix from the chamber of the first syringe.

19 Claims, 7 Drawing Sheets

METHOD OF PREPARING A GEL MATRIX FOR GRAFTING TO A BONE

CROSS REFERENCE TO RELATED APPLICATION(S)

This application claims the benefit of U.S. Provisional Application Ser. No. 61/259,411 which was filed on Nov. 9, 2009, the contents of which are incorporated by reference in its entirety.

FIELD OF THE INVENTION

The present invention relates to a method of preparing and applying grafting material to a bone. More particularly, the present invention relates to a method of preparing a gel matrix as a bone graft material and applying the gel matrix to a damaged portion of bone.

BACKGROUND OF THE INVENTION

There are many instances in which a human bone becomes damaged or deficient, typically due to either arthritis or a traumatic injury. A bone may also show signs of wear due to repetitive use over time.

It is now becoming relatively common for a person to have his/her bearing surface of a joint replaced with a synthetic implant to provide relief from the pain caused by contact of the damaged bearing surfaces of the bones that form the joint. When treating a traumatic injury, such as a fracture, it has also become relatively common to insert a metal rod into the bone to immobilize the fractured bone segments and allow the bone to heal properly.

At times, it may be more advantageous to graft another material onto a damaged portion of a person's bone to either repair the damage or to allow the bone the opportunity to properly heal. There are many types of grafts that can be placed onto a damaged surface of a person's bone, including an autograft, which utilizes a bone from another portion of a person's body to be grafted onto the damaged portion of the bone. An autograft material is the least likely graft to experience rejection by the body.

The next least likely type of graft to be rejected is an allograft, which consists of grafting a portion of another person's bone onto the damaged bone of a patient. Unlike an autograft, which takes bone from the same person to be grafted onto the same person's damaged bone, an allograft is contains material from another human's bone that can be grafted onto the damaged surface of a patient's bone.

A xenograft is a graft of a bone from another species into a patient. One typical xenograft would be, for instance, utilizing a bovine bone to graft onto a human bone. There are other types of grafts that can be utilized, such as synthetic or artificial bones made out of calcium phosphate or a combination of bioglass with calcium phosphate. Finally, plastics may also be utilized as a bone graft.

SUMMARY OF THE INVENTION

The present invention generally relates to a method of preparing a gel matrix for application as a grafting material that is used to repair damage to patient's bone. The method includes utilizing a device that includes a syringe having a continuous sidewall defining chamber where the syringe has an open top end and an open bottom end. A adapter is removably attached to the bottom end of the syringe to constrict the opening of the second end and also to provide a path for fluid communication with the chamber.

A funnel is optionally positioned on a top end of the syringe to provide a larger opening through which a selected amount of solid grafting material deposited into the chamber through the funnel. The funnel is then optionally removed from the chamber.

A plunger is inserted into the chamber at a selected position to provide a selected volume between the distal end of the syringe and a distal end of the plunger. The distal end of the plunger forms a seal with an interior surface of the chamber. The selected position is defined by the volume required to produce a selected amount of a bone graft material. The distal end of the plunger includes at least one aperture which is typically covered by a filter.

A liquid biomaterial is forced into the chamber through an opening in the adapter such that the chamber is filled with a combination of the solid grafting material and the liquid biomaterial. As the biomaterial is filled into the chamber, any gas, such as air, in the chamber is forced out of the chamber through the filter and the at least one aperture in the distal end of the plunger.

The liquid biomaterial and the solid bone graft material are retained within the chamber for a selected amount of time, such that the biomaterial and the solid bone graft material form a gel matrix. After the gel matrix is formed, the adapter is removed from the bottom end of the syringe to provide an unobstructed opening. The device is then moved to a selected surgical site having exposed damaged bone and the plunger is depressed such that the gel matrix comprising the gelled biomaterial and the solid bone graft material is forced from the chamber and onto the damaged bone surface. The gel matirx is then formed into the desired configuration on the bone to repair the surface of the bone.

DETAILED DESCRIPTION

Figure 1:
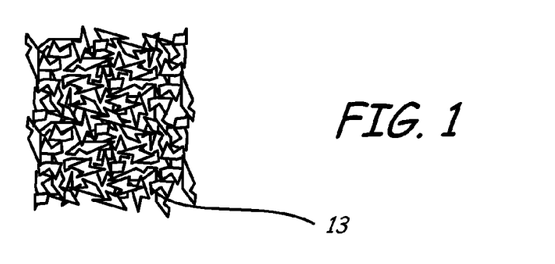
FIG. 1 is schematic view of a solid bone graft material.
Figure 2:
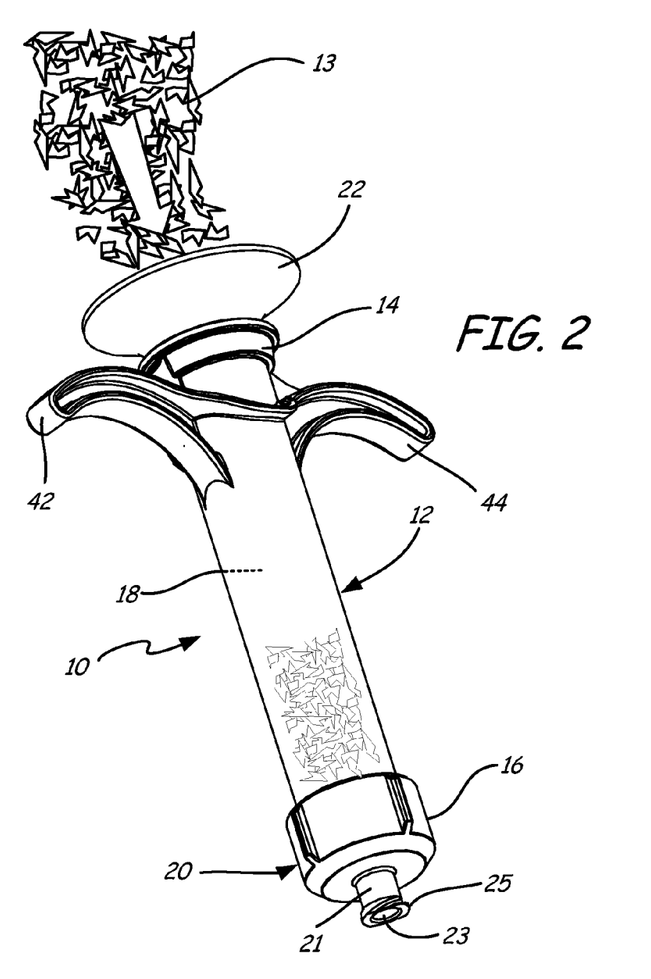
FIG. 2 is a schematic view of the solid bone graft material being disposed within a chamber of a syringe.

A bone graft delivery device is generally illustrated in FIG. 2 at 10. The bone graft delivery device includes a syringe body 12 having a proximal end 14 and a distal end 16 which define a chamber 18.

Referring to FIGS. 1-7, the bone graft delivery device 10 accepts a solid bone graft material 13 that can be inserted into the cavity 18 through the proximal end 14. The device 10 includes an adapter 20 that is removably attached to the distal end 16 of the syringe body 12. The adapter 20 includes a through bore 23 through which a liquid biomaterial 15 is transferred into the chamber 18. The liquid biomaterial 15 and the solid bone graft material 13 form a gel matrix 17 over a selected amounted of time. Once the liquid biomaterial 15 and the solid bone graft material 13 form the gel matrix 17, the adapter 20 is removed and a plunger 26 is depressed to force the gel matrix 17 from the chamber 18 for application to a bone surface to repair damage to the bone.

Referring to FIG. 2, a funnel 22 is removably inserted into the proximal end 14 of the syringe body 12. The funnel 22 has a opening 24 that has a larger diameter than the diameter of the opening at the proximal end 14 of the chamber 18. The funnel is utilized to assist in depositing the solid bone graft material 13 into the chamber 18. Once a desired amount of the solid bone graft material 13 is deposited within the chamber 18, the funnel 22 may optionally be removed from the proximal end 14 or, alternatively, the funnel 22 may remain within the proximal end 14 of the syringe body 12.

The solid bone graft material 13 is typically fragments or chips from bone form the person having the bone graft procedure. Allograft or xenograft bone chips or fragments can also be utilized as the solid bone graft material 13. A synthetic material, which is typically calcium phosphate or a combination of bioglass with calcium phosphate, can also be utilized as the solid bone graft material 13.

Figure 3:
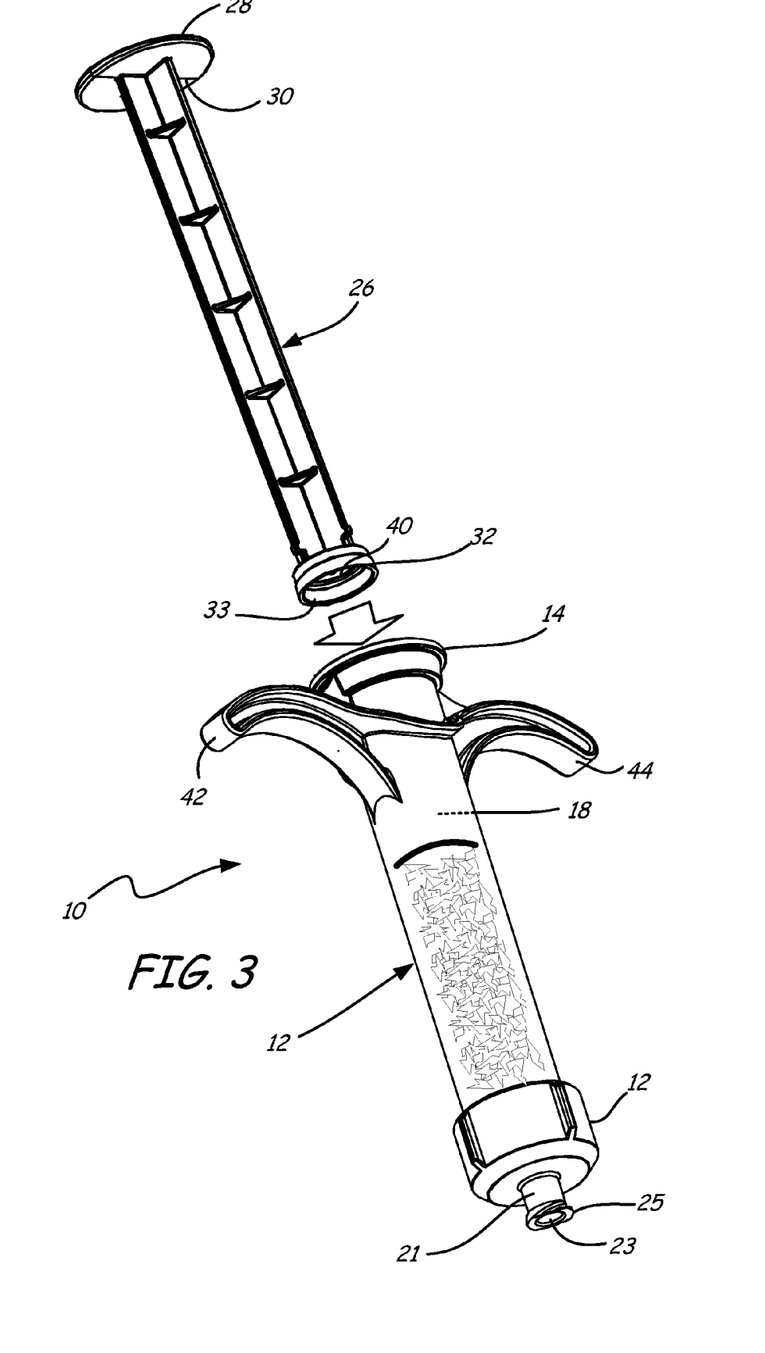
FIG. 3 is a schematic view of a plunger being inserted into a chamber of the syringe.

Once the selected amount of the solid bone graft material 13 is placed within the cavity 18, the plunger 26 is inserted within the chamber 18 as illustrated in FIG. 3. The plunger 26 can optionally be utilized to compact the bone graft material as indicated by arrows 31 in FIG. 4.

Figure 4:
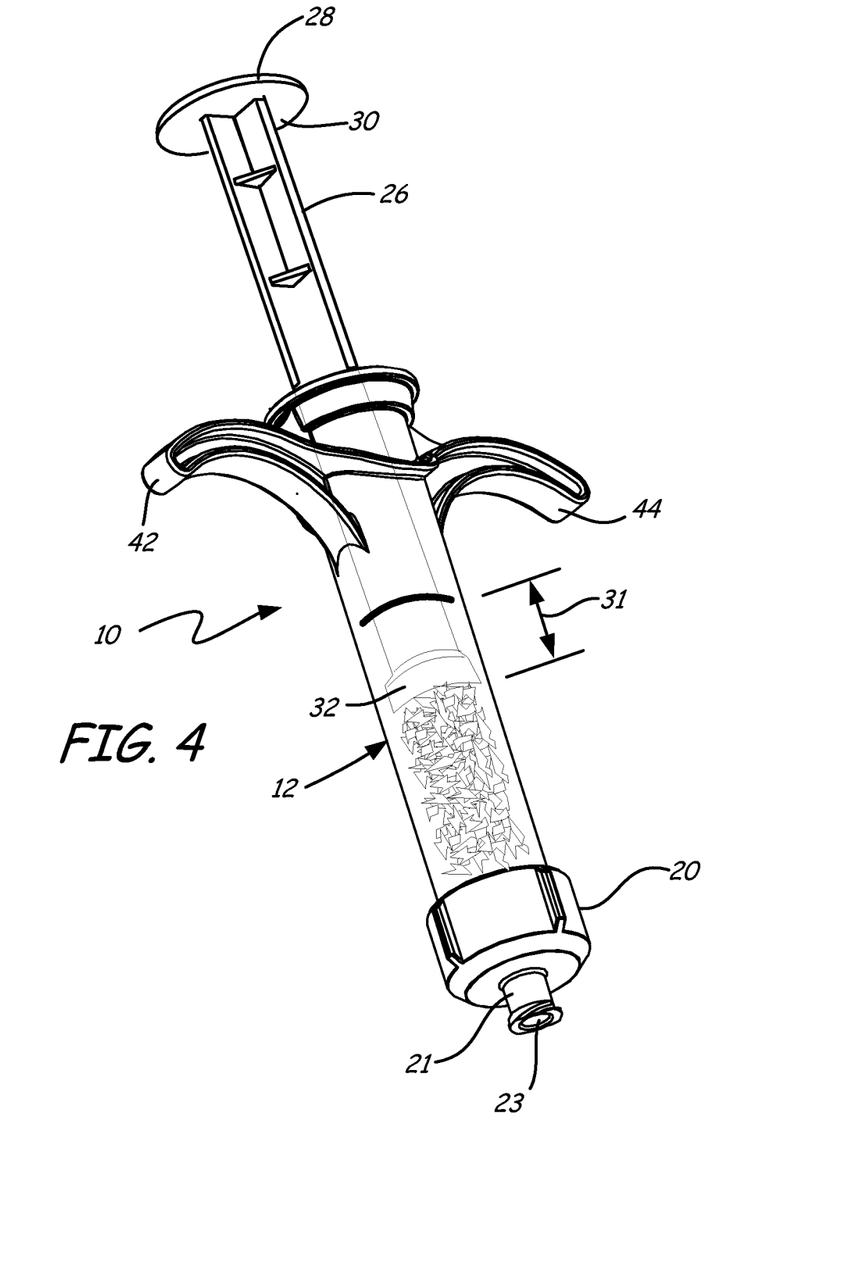
FIG. 4 is a schematic view of the plunger compacting the solid bone graft material.

Referring to FIGS. 3-4, the plunger 26 includes a plunger head 28 that is utilized to force the plunger 26 into the chamber 18. The plunger head 28 is located at a proximal end 30 of the plunger 26. A distal end 32 of the plunger includes a cavity 33 that accepts a filter (not shown). A retention ring (not shown) is positioned within the cavity (not shown) such that the filter is retained within the cavity 33 during use and the filter is not allowed to accidentally be displaced from the cavity.

The distal end 32 of the plunger form a seal with an interior surface of the chamber 18. The distal end 32 includes at least one aperture 40 that allows gases to vent from the chamber 18 as the liquid biomaterial 15 is forced into the chamber 18.

Figure 5:
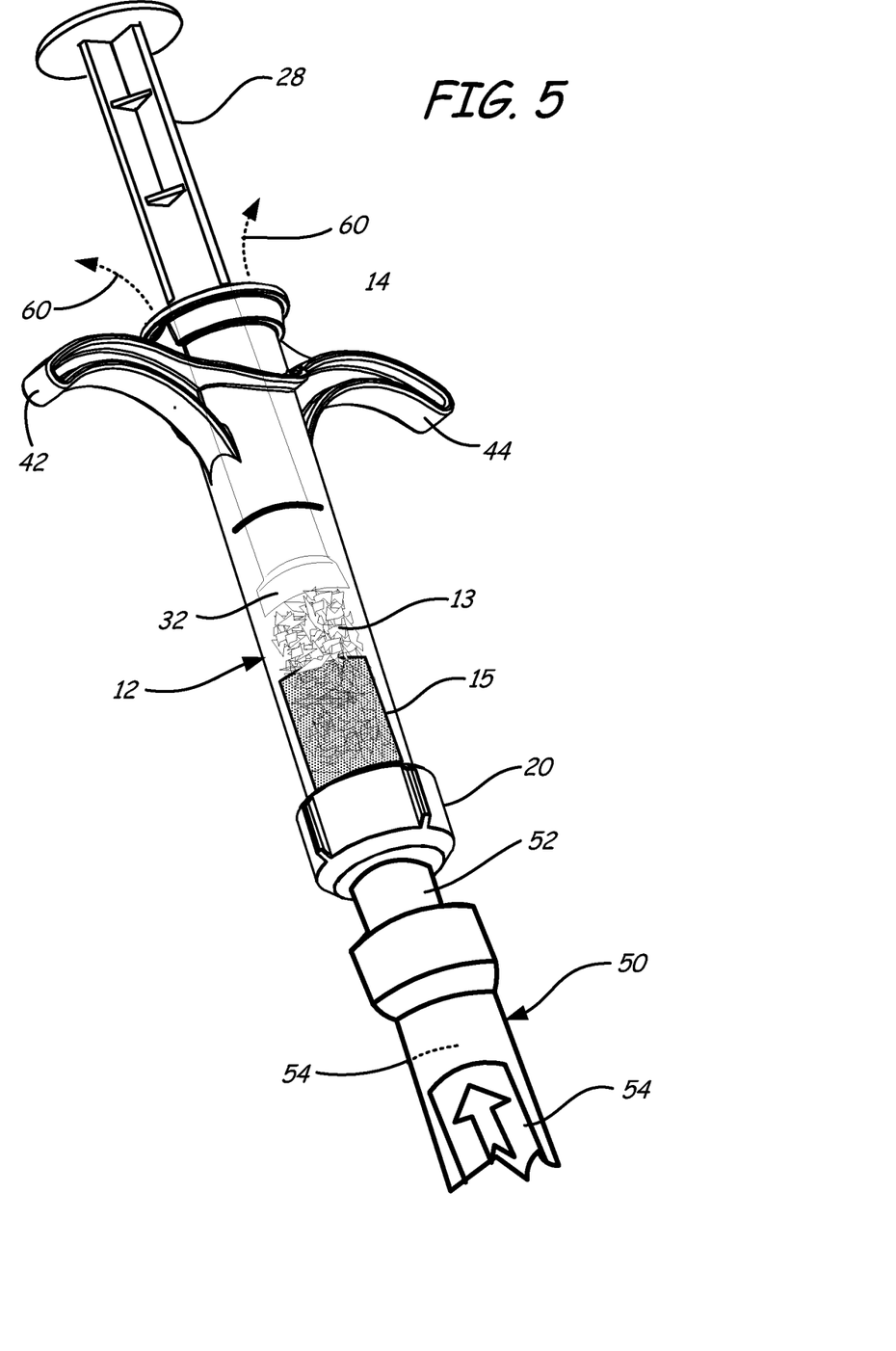
FIG. 5 is a schematic view of a liquid biomatertial being disposed into the chamber of the syringe and displacing air from the chamber.

Referring to FIGS. 3 and 5, with the distal end 32 of the plunger 26 in the selected position within the chamber 18, the liquid biomaterial 15 is transferred into the chamber 18 through the adapter 20. The adapter 20 includes the inlet port 21 having the throughbore 23 that is in fluid communication with the chamber 18. The liquid biomaterial 15 is then forced into the cavity 18 through the throughbore 23.

The adapter 20 includes a Luer connection 25 on an exterior surface of the inlet port 21. A second syringe 50 having a complementary portion 52 of a Luer connector is secured to the inlet port 21 such that a second chamber 54 of the second syringe 50 is in fluid communication with the chamber 18 of the device 10 through the throughbore 23 of the adapter 20. Other connecting mechanisms besides a Luer connection are also contemplated.

A plunger 54 is depressed to force the liquid biometerial 15 into the chamber 18. While a single chamber syringe 50 is illustrated, it is also contemplated that a multichamber syringe 50 could be utilized to segregate biomaterials that once combined form a gel from mixing until the materials are forced into the chamber 18 of the device 10.

As the liquid biomaterial 15 is transferred into the cavity 18, air is displaced out of the chamber 18 through the filter 34 and the at least one apertures 40 in the distal end 32 of the plunger as best illustrated at arrows 60 in FIG. 5. As all of the gas is displaced from the chamber 18, the chamber 18 contains the liquid biomaterial 15 and the solid bone graft material 13 in a mixture without voids where the solid bone graft material 13 is dispersed within the liquid biomaterial 15.

Figure 6:
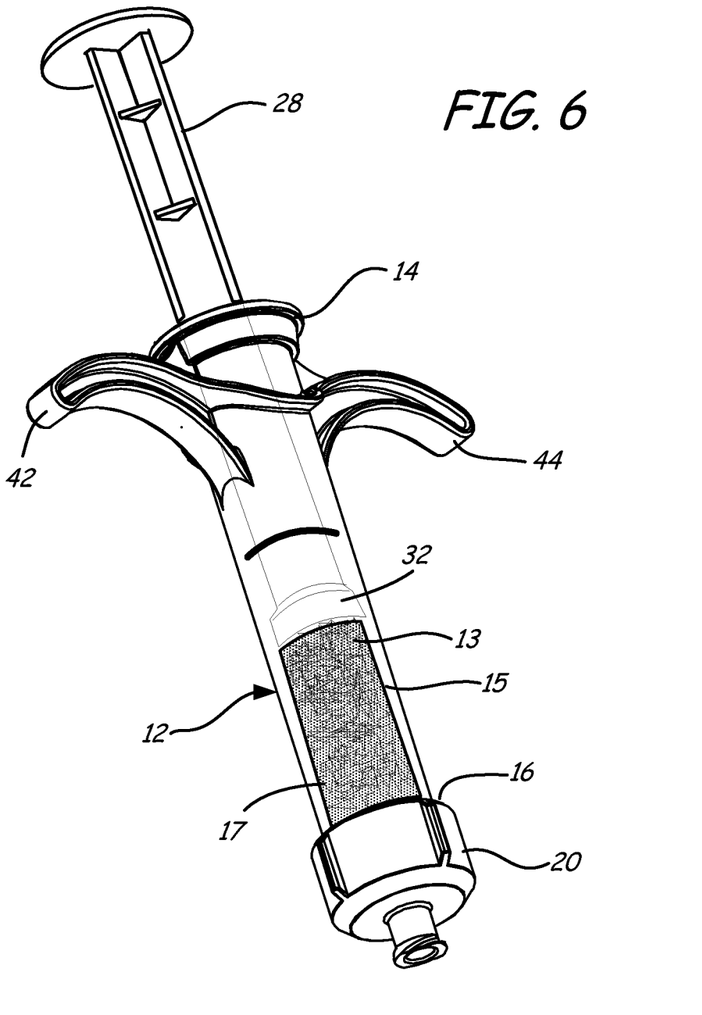
FIG. 6 is a schematic view of the liquid biomaterial and the solid bone graft material forming a gel matrix.

Referring to FIG. 6, the mixture of the solid bone graft material 13 and the liquid biomaterial 15 is retained within the cavity 18 for a selected amount of time such that the liquid biomaterial 15 forms a gel matrix 17 that contains the solid bone graft material 13. Typical liquid biomaterials include platelet concentrate, autologous blood, bone marrow aspirate or other blood component(s) or combinations thereof as deemed necessary by the clinical requirements.

Figure 7:
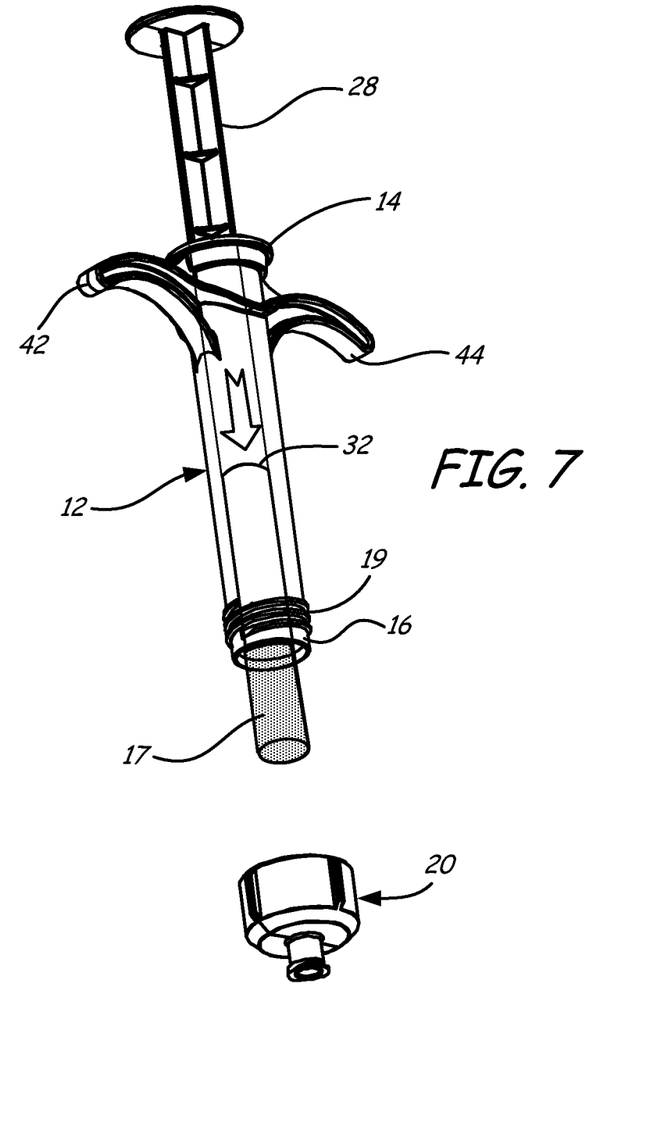
FIG. 7 is a schematic view of the gel matrix being forced out of the chamber of the syringe.

Referring to FIG. 7, once the gel matrix 17 has formed, the adapter 20 is threadably disengaged from the threads 19 on the outer surface of the syringe body 12. Removing the adapter 20 provides an unobstructed or non-constricted opening at the distal end 16 such that the gel matrix 17 can be forced from the syringe body 12 for application to a surgical site. While a threaded engagement of the adapter 20 and the syringe body 12 is illustrated, other connecting mechanisms are also contemplated.

The gel matrix is displaced from the cavity 18 by depressing the plunger 26 into the cavity 18 with manual force placed upon the plunger head 28. Finger grips 42, 44 extend from opposite side of the syringe body 12 to provide an opposing surface for medical personnel to grip the syringe body 12 and place the manual force upon the plunger head 28 which forces the gel matrix 17 from the chamber 18. Once the gel matrix 17 has been displaced from the syringe body 12, the gel matrix 17 is then placed in the desired position on the person's body to graft the bone chips to the defective bone.

Figure 8:
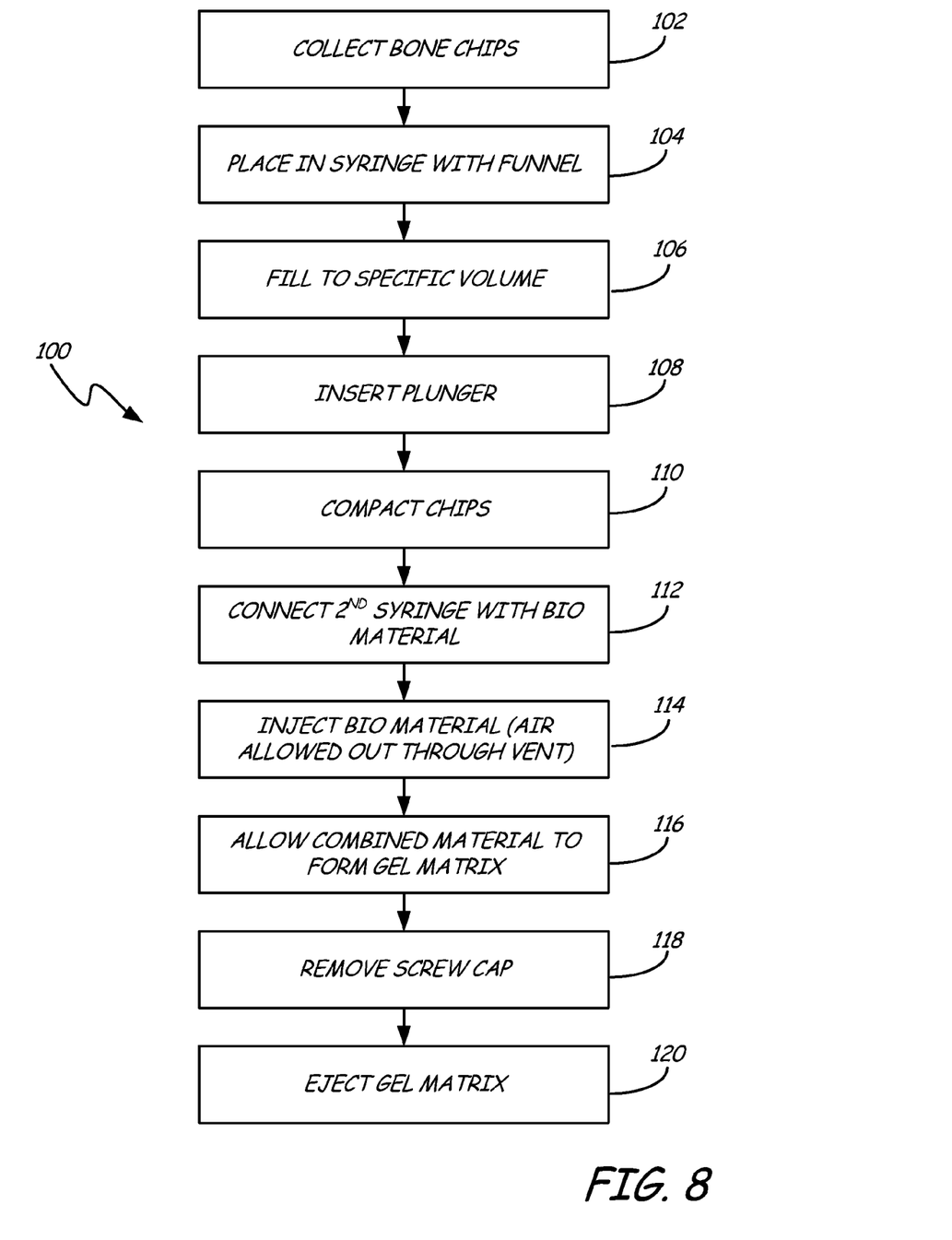
FIG. 8 a flow chart of a method for preparing a gel matrix made from a solid bone graft material and a liquid biomaterial for grafting to a bone.

Referring to FIG. 8, a flow chart 100 of for utilizing the method of utilizing autograft solid bone graft material in a gel matrix is described. Bone chips or fragments are collected during a surgical procedure at step 102. A funnel is optionally placed into a syringe and the bone fragment or chips are placed into the syringe through the funnel at step 104. A selected amount of bone chips or fragments are placed into the syringe at step 106.

A plunger is inserted into the syringe at step 108. The bone chips or fragments are optionally compacted with a plunger in step 110.

A second syringe containing a liquid biomaterial is connected to the first syringe at step 112. The biomaterial is injected into the first syringe while venting air from the first syringe at step 114. The biomaterial and bone chips or fragments are retained in the first syringe for a selected amount of time to form a gel matrix at step 116.

The adapter is removed form the distal end of the syringe at step 118 to provide an unobstructed opening at the distal end of the syringe. The plunger is depressed to force the gel matrix from the syringe at step 120. The gel matrix is then applied as a grafting material to the desire location on a bone.

Although the present invention has been described with reference to preferred embodiments, workers skilled in the art will recognize that changes may be made in form and detail without departing from the spirit and scope of the invention.

What is claimed is:

1. A method of preparing a graft material for a bone surface, the method comprising:
   providing a first syringe having continuous side wall having an inner surface and an outer surface wherein the syringe has a first end and a second end wherein the inner surface defines a chamber;
   attaching an adapter to the distal end of the syringe wherein the adapter has a throughbore in fluid communication with the chamber;

disposing a first selected amount of solid bone graft material within the chamber;

inserting a plunger into the chamber to define a selected volume between the distal end of the plunger and the second end of the first syringe;

connecting a second syringe containing a selected amount of a liquid biomaterial to the adapter wherein the second syringe is in fluid communication with the adapter and the first syringe;

transferring the liquid biomaterial from the second syringe to the first syringe;

venting air through the plunger as the biomaterial is transferred to the first syringe;

providing a selected amount of time for the liquid biomaterial to form a gel and a gel matrix containing the solid bone graft material;

removing the adapter to provide an unobstructed opening; and depressing the plunger to force the gel matrix from the chamber of the first syringe.

2. The method of claim 1 and wherein disposing a first selected amount of solid bone graft material within the chamber comprises disposing a first selected amount of allograft bone chips or fragments into the chamber.

3. The method of claim 1 and wherein disposing a first selected amount of solid bone graft material within the chamber comprises disposing a first selected amount of autograft bone chips or fragments into the chamber.

4. The method of claim 1 and wherein disposing a first selected amount of solid bone graft material within the chamber comprises disposing a first selected amount of xenograft solid bone graft material into the chamber.

5. The method of claim 4 and wherein the xenograft material comprises calcium phosphate.

6. The method of claim 4 and wherein the xenograft material comprises a combination of bioglass and calcium phosphate.

7. The method of claim 1 and wherein transferring the liquid biomaterial from the second syringe to the first syringe comprises depressing a second plunger in the second syringe to transfer the liquid biomaterial into the chamber of the first syringe.

8. The method of claim 1 and wherein transferring the liquid biomaterial from the second syringe to the first syringe comprises transferring platelet concentrate, autologous blood, bone marrow aspirate or other blood components or combinations thereof.

9. The method of claim 1 and wherein when the selected amount of a liquid biomaterial is transferred to the chamber of the first syringe, no air remains in the interior compartment.

10. The method of claim 1 and wherein the adapter is removed and attached to the first syringe through a threaded engagement between the adapter and the outer surface of the continuous side wall.

11. A method of preparing and delivering a graft material to a bone surface at a surgical site, the method comprising:

providing a first syringe having a continuous side wall having an inner surface and an outer surface wherein the syringe has a first end and a second end wherein the inner surface defines a chamber;

attaching an adapter to the distal end of the syringe wherein the adapter has a throughbore in fluid communication with the chamber;

disposing a first selected amount of solid bone graft material within the chamber;

inserting a plunger into the chamber to define a selected volume between the first end and the second end of the first syringe;

forcing a selected amount of a liquid biomaterial into the chamber through the throughbore in the adapter;

venting air from the chamber through an aperture in the plunger as the liquid biomaterial is forced into the chamber;

providing a selected amount of time for the liquid biomaterial to form a gel and a gel matrix containing the solid bone graft material;

removing the adapter to provide an unconstricted opening;

depressing the plunger to force the gel matrix from the chamber of the syringe; and applying the gel matrix to the bone surface at the surgical site.

12. The method of claim 11 and wherein forcing a selected amount of a liquid biomaterial into the chamber through the throughbore in the adapter comprises:

connecting a second syringe containing the selected amount of the liquid biomaterial to the adapter wherein the second syringe is in fluid communication with the adapter and the first syringe;

transferring the liquid biomaterial from the second syringe to the first syringe.

13. The method of claim 11 and wherein disposing a first selected amount of solid bone graft material within the chamber comprises disposing a first selected amount of allograft bone chips or fragments into the chamber.

14. The method of claim 11 and wherein disposing a first selected amount of solid bone graft material within the chamber comprises disposing a first selected amount of autograft bone chips or fragments into the chamber.

15. The method of claim 11 and wherein disposing a first selected amount of solid bone graft material within the chamber comprises disposing a first selected amount of xenograft solid bone graft material into the chamber.

16. The method of claim 15 and wherein the xenograft material comprises calcium phosphate.

17. The method of claim 15 and wherein the xenograft material comprises a combination of bioglass and calcium phosphate.

18. The method of claim 11 and wherein forcing a selected amount of a liquid biomaterial into the chamber comprises forcing platelet concentrate, autologous blood, bone marrow aspirate or other blood components or combinations thereof into the chamber.

19. The method of claim 11 and wherein the adapter is removed and attached to the first syringe through a threaded engagement between the adapter and the outer surface of the continuous side wall.

* * * * *